US012616853B2

(12) United States Patent
    Lin

(10) Patent No.: US 12,616,853 B2
(45) Date of Patent: May 5, 2026

(54) PATIENT-POSITIONING SYSTEM FOR RADIOTHERAPY

(71) Applicant: Heron Neutron Medical Corp., Zhubei City (TW)

(72) Inventor: Tzung-Yi Lin, Zhubei City (TW)

(73) Assignee: HERON NEUTRON MEDICAL CORP., Zhubei City (TW)

( * ) Notice: Subject to any disclaimer, the term of this patent is extended or adjusted under 35 U.S.C. 154(b) by 366 days.

(21) Appl. No.: 18/333,182

(22) Filed: Jun. 12, 2023

(65) Prior Publication Data

US 2024/0245934 A1     Jul. 25, 2024

(30) Foreign Application Priority Data

Jan. 19, 2023    (TW) ................................. 112102560

(51) Int. Cl.
    *A61N 5/10*          (2006.01)
    *G16H 20/40*         (2018.01)
(52) U.S. Cl.
    CPC ........... *A61N 5/1049* (2013.01); *G16H 20/40* (2018.01); *A61N 2005/105* (2013.01); *A61N 2005/1059* (2013.01)
(58) Field of Classification Search
    None
    See application file for complete search history.

(56) References Cited

U.S. PATENT DOCUMENTS

2004/0172145 A1     9/2004    Varadharajulu
2007/0284543 A1    12/2007    Rockseisen 2010/0208274 A1     8/2010    Kindlein et al.
2013/0156152 A1     6/2013    Boda et al.
2015/0045676 A1     2/2015    Dawson et al.
2018/0353774 A1    12/2018    Meir et al.
(Continued)

FOREIGN PATENT DOCUMENTS

CN     114723790 A        7/2022
JP     2019-141581    *   8/2019
JP     2019-141581 A      8/2019
(Continued)

OTHER PUBLICATIONS

Extended European Search Report for European Application No. 23183831.9, dated Dec. 19, 2023.
(Continued)

*Primary Examiner* — Hoon K Song
(74) *Attorney, Agent, or Firm* — Birch, Stewart, Kolasch & Birch, LLP

(57)            ABSTRACT

A patient-positioning system for radiotherapy is provided. The system includes a processing device and a storage device. The processing device loads a program from the storage device to execute a control module, a positioning room module, and a treatment room module. The control module obtains treatment planning data. The positioning room module calculates the second support displacement of the fulcrum through image registration based on the tilt angle, rotation angle, target displacement, original target point cloud, and a reference displacement. The treatment room module drives the mechanical device to move the treatment room table such that the fulcrum is at the second support displacement relative to the beam exit.

9 Claims, 11 Drawing Sheets

(56)              References Cited

U.S. PATENT DOCUMENTS

| | | |
|---|---|---|
| 2019/0099144 A1 | 4/2019 | Rieger et al. |
| 2020/0184625 A1 | 6/2020 | Meir et al. |

FOREIGN PATENT DOCUMENTS

| | | |
|---|---|---|
| JP | 2019-154671 A | 9/2019 |
| JP | 2019-166098 A | 10/2019 |
| WO | WO 2019/116678 A1 | 6/2019 |

OTHER PUBLICATIONS

Japanese Office Action for Japanese Application No. 2023-191123, dated Aug. 20, 2024, with an English translation.

* cited by examiner

300

305C

304C

305B

304B

301

302

304A

305A

303

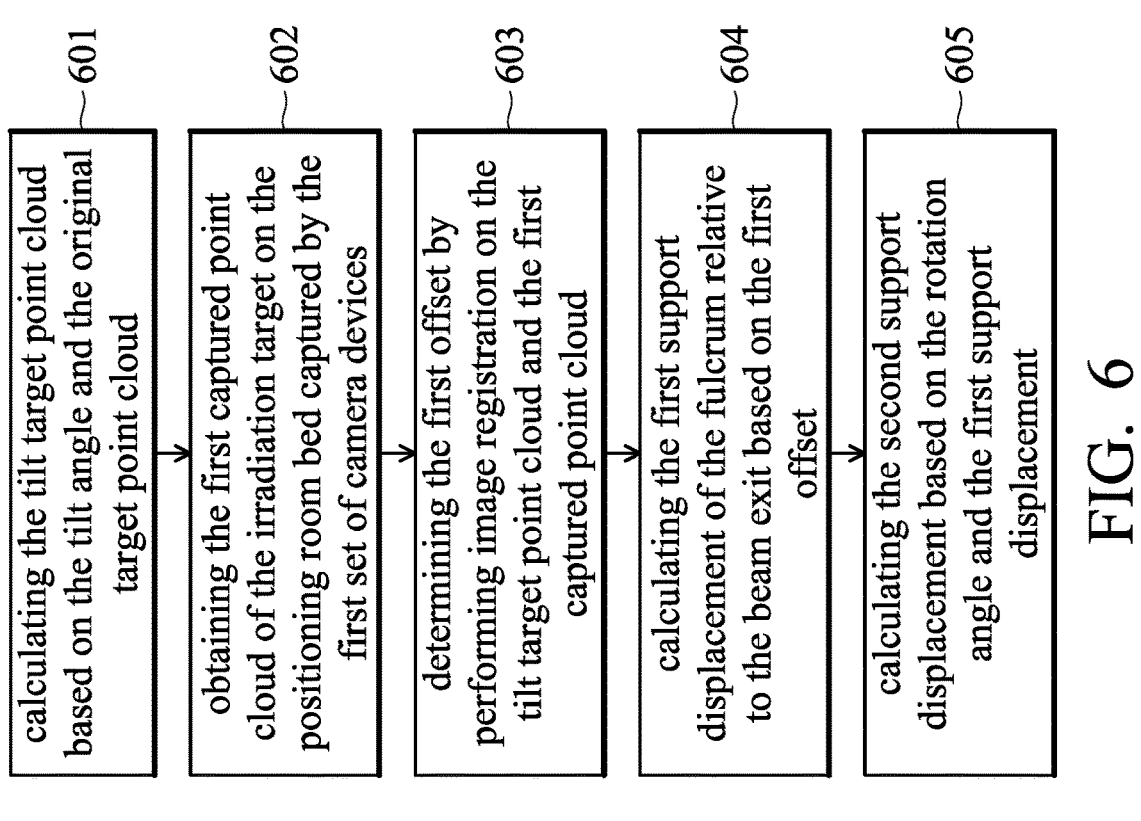

203 calculating the tilt target point cloud based on the tilt angle and the original target point cloud 〜601 obtaining the first captured point cloud of the irradiation target on the positioning room bed captured by the first set of camera devices 〜602 determining the first offset by performing image registration on the tilt target point cloud and the first captured point cloud 〜603 calculating the first support displacement of the fulcrum relative to the beam exit based on the first offset 〜604 calculating the second support displacement based on the rotation angle and the first support displacement 〜605

FIG. 6

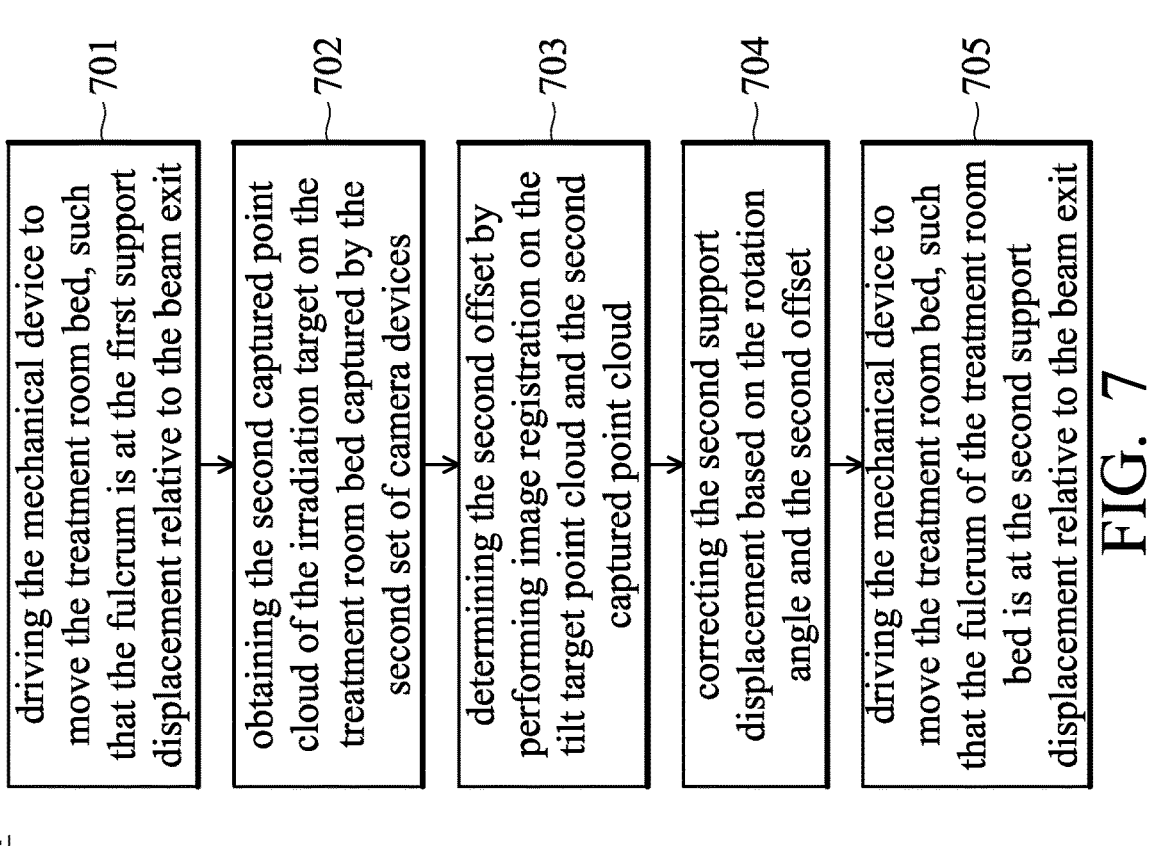

204

701 — driving the mechanical device to move the treatment room bed, such that the fulcrum is at the first support displacement relative to the beam exit 702 — obtaining the second captured point cloud of the irradiation target on the treatment room bed captured by the second set of camera devices 703 — determining the second offset by performing image registration on the tilt target point cloud and the second captured point cloud 704 — correcting the second support displacement based on the rotation angle and the second offset 705 — driving the mechanical device to move the treatment room bed, such that the fulcrum of the treatment room bed is at the second support displacement relative to the beam exit

FIG. 7

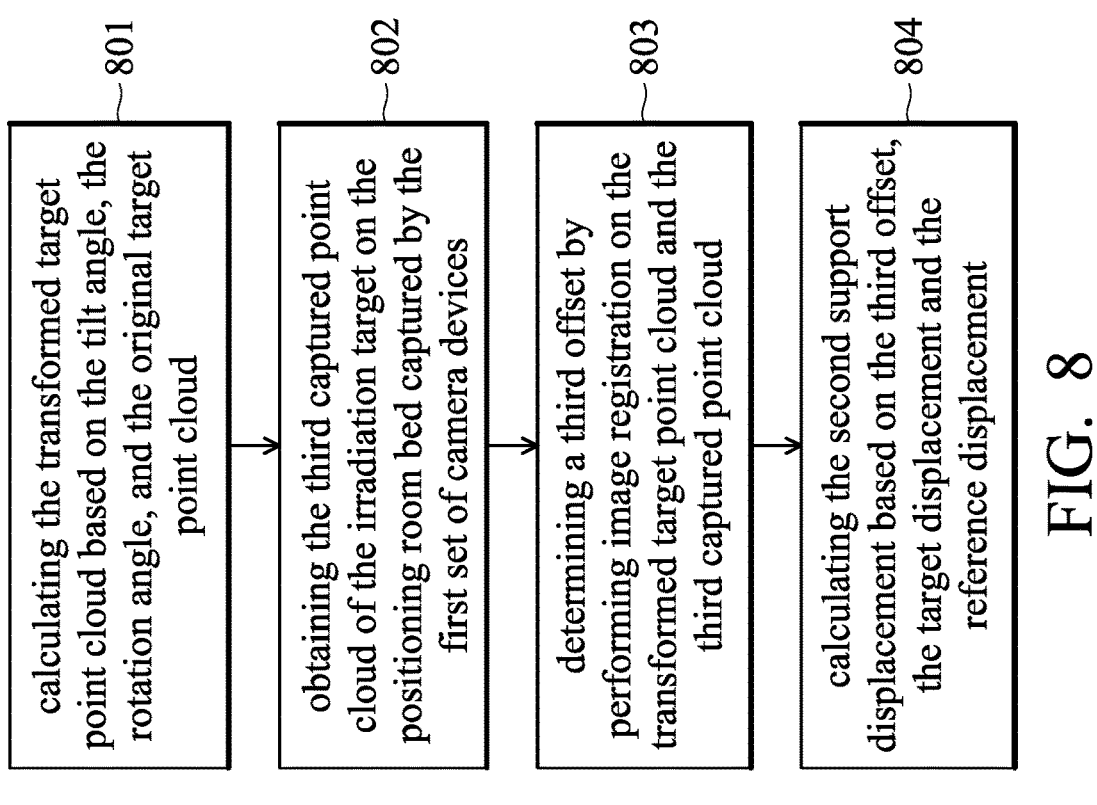

203R

801 — calculating the transformed target point cloud based on the tilt angle, the rotation angle, and the original target point cloud 802 — obtaining the third captured point cloud of the irradiation target on the positioning room bed captured by the first set of camera devices 803 — determining a third offset by performing image registration on the transformed target point cloud and the third captured point cloud 804 — calculating the second support displacement based on the third offset, the target displacement and the reference displacement

FIG. 8

206 obtaining the fourth captured point cloud of the calibration object on the bed 401 in the treatment room — 901 calibrating the parameter settings of the second set of camera devices by performing image registration on the fourth captured point cloud and the calibration object point cloud — 902

PATIENT-POSITIONING SYSTEM FOR RADIOTHERAPY

CROSS REFERENCE TO RELATED APPLICATIONS

This Application claims priority of Taiwan Patent Application No. 112102560, filed on Jan. 19, 2023, the entirety of which is incorporated by reference herein.

BACKGROUND OF THE INVENTION

Field of the Invention

The present disclosure relates in general to the field of radiotherapy, and it relates in particular to a patient-positioning system for radiotherapy.

Description of the Related Art

In the field of radiation therapy (which includes procedures such as Boron Neutron Capture Therapy (BNCT)), it may be necessary for patients to be irradiated in various postures. Therefore, the table on which a patient is lying during such radiation therapy can not only be rotated on the horizontal plane, but it can also be tilted in the vertical direction. Currently, patient-positioning systems for radiotherapy use, as input data, computed tomography (CT) images taken of the patient in the supine position before radiotherapy. Based on this, the image monitoring and analysis of the patient's surface characteristics are performed to locate the affected part of the patient (i.e., to learn the relative spatial position of the irradiation target). If the patient needs to be irradiated in other postures, the patient table may have various tilt angles or rotation angles for accurately irradiating the patient, and the position of the patient's affected part (i.e., the irradiation target) will inevitably change relative to the supine posture. However, suitable solutions for positioning patients in various postures are currently lacking.

In view of the above problems, there is a need for a patient-positioning system for radiotherapy that takes into account the rotation angle and tilt angle of the patient table, so as to more accurately locate the irradiation target.

BRIEF SUMMARY OF THE INVENTION

An embodiment of the present disclosure provides a patient-positioning system for radiotherapy. The system includes a processing device and a storage device. The processing device loads a program from the storage device to execute a control module, a positioning room module, and a treatment room module. The control module obtains treatment planning data. The treatment planning data includes the tilt angle, rotation angle, target displacement, and the original target point cloud of an irradiation target. The positioning room module calculates the second support displacement of the fulcrum through image registration based on the tilt angle, rotation angle, target displacement, original target point cloud, and a reference displacement. The second support displacement is the displacement of the fulcrum relative to the beam exit when the arrangement of a treatment room table conforms to the treatment planning data. The treatment room table and a mechanical device are connected at the fulcrum. The treatment room module drives the mechanical device to move the treatment room table such that the fulcrum is at the second support displacement relative to the beam exit. When the arrangement of the treatment room table conforms to the treatment planning data, the treatment room table is tilted at the tilt angle and rotated at the rotation angle, and the irradiation target on the treatment room table is at the target displacement relative to the beam exit.

In an embodiment, the positioning room module further calculates a tilt target point cloud based on the tilt angle and the original target point cloud. The positioning room module further obtains a first captured point cloud of the irradiation target on the positioning room table. The first captured point cloud is captured by a first set of camera devices when the positioning room table is tilted at the tilt angle. The positioning room module further determines a first offset by performing image registration on the tilt target point cloud and the first captured point cloud. The positioning room module further calculates the first support displacement of the fulcrum based on the first offset, the target displacement, and the reference displacement. The first support displacement is the displacement of the fulcrum relative to the beam exit when the treatment room table is tilted at the tilt angle but not rotated. The positioning room module further calculates the second support displacement based on the rotation angle and the first support displacement.

In an embodiment, the treatment room module further drives the mechanical device to move the treatment room table such that the fulcrum is at the first support displacement relative to the beam exit. The treatment room module further obtains a second captured point cloud of the irradiation target on the treatment room table. The second captured point cloud is captured by a second set of camera devices when the treatment room table is tilted at the tilt angle. The treatment room module further determines a second offset by performing image registration on the tilt target point cloud and the second captured point cloud. The treatment room module further corrects the second support displacement based on the rotation angle and the second offset.

In an embodiment, the treatment room module further obtains a fourth captured point cloud of a calibration object on the treatment room table. The fourth captured point cloud is captured by the second set of camera devices. The treatment room module further calibrates parameter settings of the second set of camera devices by performing image registration on the fourth captured point cloud and a calibration object point cloud. A second set of laser emitters are attached to the second set of camera devices. When the second set of camera devices captures the fourth captured point cloud, laser beams emitted by the second set of laser emitters are aligned with corresponding crosshairs on the calibration object.

In an embodiment, the positioning room module further calculates a transformed target point cloud based on the tilt angle, the rotation angle and the original target point cloud. The positioning room module further obtains a third captured point cloud of the irradiation target on the positioning room table. The third captured point cloud is captured by the first set of camera devices when the positioning room table is tilted at the tilt angle and rotated at the rotation angle. The positioning room module further determines a third offset by performing image registration on the transformed target point cloud and the third captured point cloud. The positioning room module further calculates the second support displacement based on the third offset, the target displacement, and the reference displacement.

In an embodiment, the positioning room module further obtains a fifth camera point cloud of a calibration object on the positioning room table. The fifth camera point cloud is captured by the first set of camera devices. The positioning room module further calibrates parameter settings of the first set of camera devices by performing image registration on the fifth captured point cloud and the calibration object point cloud. A first set of laser emitters are attached to the first set of camera devices. When the first set of camera devices captures the fifth captured point cloud, laser beams emitted by the first set of laser emitters are aligned with corresponding crosshairs on the calibration object.

In an embodiment, the treatment room module further drives the mechanical device to move the treatment room table such that the calibration object on the treatment room table is at the target displacement relative to the beam exit. The treatment room module further obtains the third support displacement of the fulcrum relative to the beam exit. The treatment room module further calculates the reference displacement of the fulcrum relative to the calibration object based on the third support displacement and the target displacement.

In an embodiment, the treatment room module further drives the irradiation device to irradiate the irradiation target on the patient table.

The patient-positioning system provided in the present disclosure increases the consideration and adjustment of the tilt and rotation angle of the patient table/chair and the irradiation direction, enabling more efficient and accurate irradiation of the patient's affected part in the context of radiotherapy.

BRIEF DESCRIPTION OF THE DRAWINGS

The present disclosure can be more fully understood by reading the subsequent detailed description and examples with references made to the accompanying drawings. Additionally, it should be appreciated that in the flow diagram of the present disclosure, the order of execution for each blocks can be changed, and/or some of the blocks can be changed, eliminated, or combined.

FIG. 6 is a flow diagram of the positioning room positioning process of the first implementation, according to an embodiment of the present disclosure;

FIG. 7 is a flow diagram of a treatment room positioning process, according to an embodiment of the present disclosure;

FIG. 8 is a flow diagram of the positioning room positioning process in the second implementation, according to another embodiment of the present disclosure;

FIG. 9 is a flow diagram of the camera parameter calibration process, according to an embodiment of the present disclosure;

DETAILED DESCRIPTION OF THE INVENTION

Figure 1:
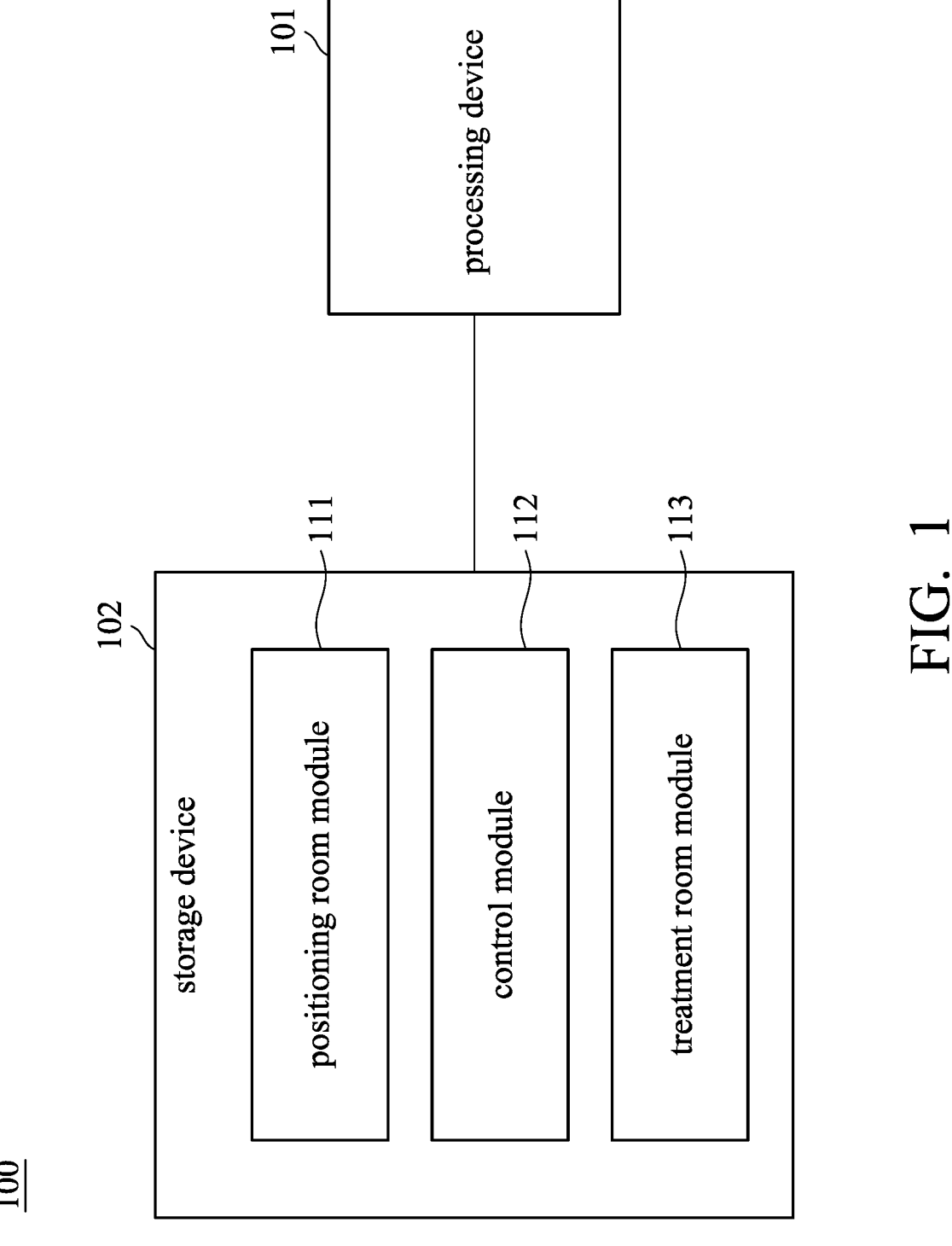
FIG. 1 is a hardware architecture diagram of a patient-positioning system for radiotherapy, according to an embodiment of the present disclosure.

The following description is made for the purpose of illustrating the general principles of the invention and should not be taken in a limiting sense. The scope of the invention is determined by reference to the appended claims.

In each of the following embodiments, the same reference numbers represent identical or similar elements or components.

Ordinal terms used in the claims, such as "first," "second," "third," etc., are only for convenience of explanation, and do not imply any precedence relation between one another.

First, a general introduction is given to the positioning room, treatment room and control room required for the patient-positioning system provided in the present disclosure for radiotherapy. It should be noted that terms such as "positioning room", "treatment room" and "control room" in this specification do not necessarily refer to a specific space, but may refer to a combination of hardware configuration and software configuration. It is not intended to limit the space in which these combinations locate. In various embodiments, the positioning room, treatment room, and control room may be in the same room, or in different rooms. In an embodiment, the positioning room and the treatment room may share hardware configurations in the same space, but have different software configurations.

In order to make the use of resources in the treatment room more efficient, the pre-processing procedures required before radiotherapy (including locating the relative position of the patient's affected part in space) are usually performed in the positioning room first, so that the treatment room can focus more on performing radiotherapy. Meanwhile, the control room is responsible for receiving the treatment plan, and for the communication between the positioning room and the treatment room. Specifically, the patient to be treated with radiotherapy will first go through the pre-processing procedure in the positioning room to simulate the position of the iso-center (i.e., the irradiation target, or the affected part of the patient) in the treatment plan. By using the camera device and the hardware configuration of the crosshair laser, tortuous changes of the patient's body surface are detected in order to confirm the same spatial coordinate position as the irradiation target surface. If there is a difference between the spatial positions of the two, the position of the camera device will be adjusted. The above operations are repeated until the spatial position difference between the two drops to a level that is within an acceptable range. At this moment, it means that the crosshair laser should pass through the isocenter position of the irradiation target, so the operator in the positioning room can make a mask for the patient and draw a marker on the mask. Then, the relative position of the irradiation target is transmitted to the treatment room via the control room, so that the irradiation device in the treatment room can irradiate the irradiation target.

FIG. 1 is a hardware architecture diagram of a patient-positioning system 100 for radiotherapy, according to an embodiment of the present disclosure. As shown in FIG. 1, the patient-positioning system 100 may include a processing device 101 and a storage device 102 coupled to each other. In addition, the positioning room module 111, the control module 112 and the treatment room module 113 are stored in the storage device 102.

The patient-positioning system 100 may be a personal computer (e.g., desktop or laptop) or a server computer running an operating system (e.g., Windows, Mac OS, Linux, UNIX, etc.), or a mobile device such as a tablet computer or a smart phone, but the present disclosure is not limited thereto.

The processing device 101 may be any device for executing instructions, such as a central processing unit (CPU), a graphics processing unit (GPU), a microprocessor, a controller, a microcontroller, or a state machine, but the present disclosure is not limited thereto.

The storage device 102 can be any non-volatile memory (e.g., read-only memory, electronically-erasable programmable read-only memory (EEPROM), flash memory, non-volatile random access memory (NVRAM)), such as hard disk (HDD), solid state disk (SSD) or optical disk, but the present disclosure is not limited thereto.

The positioning room module 111, the control module 112, and the treatment room module 113 are software modules. In various embodiments, the processing device 101 loads a program from the storage device 102 to execute these software modules. The program can be written in Java, C, C#, C++, Python, or any known programming language, which is not limited in the present disclosure.

In an embodiment, the patient-positioning system 100 may further include a communication interface (though not shown in FIG. 1), which allows the computer system to communicate with other devices to obtain required data. The communication interface can be a wired communication interface, such as a High Definition Multimedia Interface (HDMI), a DisplayPort (DP) interface, an embedded DisplayPort (eDP) interface, a Universal Serial Bus (USB) interface, USB Type-C interface, Thunderbolt interface, Digital Video Interface (DVI), and the combinations thereof. The communication interface can also be a wireless communication interface, the 5th generation (5G) wireless system, Bluetooth (Bluetooth), WiFi, Near Field Communication (NFC) interface, etc., but the present disclosure is not limited thereto.

Figure 2:
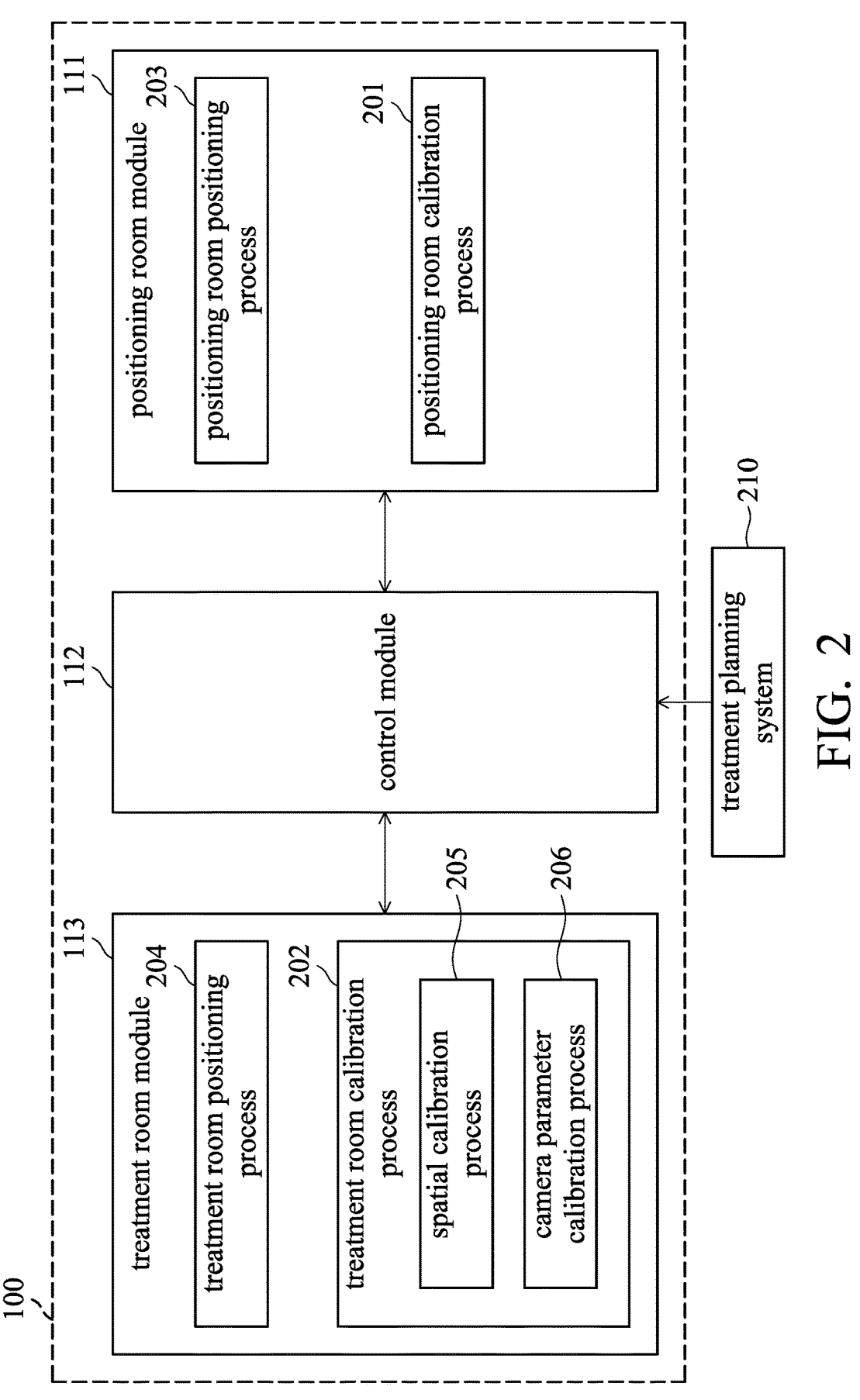
FIG. 2 is a software architecture diagram of the patient-positioning system, according to an embodiment of the present disclosure.

FIG. 2 is a software architecture diagram of the patient-positioning system 100, according to an embodiment of the disclosure. As shown in FIG. 2, the positioning room module 111 may include a positioning room positioning process 203 and a positioning room calibration process 201, and the treatment room module 113 may include a treatment room positioning process 204 and a treatment room calibration process 202. Furthermore, the treatment room calibration process 202 may include a spatial calibration process 205 and a camera parameter calibration process 206. Each of the processes 201-206 may include a plurality of steps or operation instructions, the details of which will be described in the following paragraphs together with FIG. 6-11. In addition, it should be appreciated that the positioning room module 111 and the treatment room module 113 shown in FIG. 2 are only a preferred embodiment, and the present disclosure does not limit the software architecture of the patient-positioning system 100 to include all the processes 201-206.

In an embodiment, the patient-positioning system 100 can connect to the treatment planning system 210 in a wired or wireless manner through the aforementioned communication interface, so that the control module 112 can obtain treatment planning data from the treatment planning system

210. In another embodiment, the patient-positioning system 100 can indirectly obtain the treatment planning data output by the treatment planning system 210 via a storage medium such as a mobile hard disk or cloud storage space. In addition to obtaining treatment plan information, the control module is also responsible for the communication between the positioning room module 111 and the treatment room module 113.

In various embodiments, the treatment planning data includes, but is not limited to, the tilt angle, rotation angle, target displacement, and original target point cloud of the irradiated target. The tilt angle is the angle at which the table in the treatment room (hereinafter referred to as "the treatment room table") is planned to tilt upward when the patient is undergoing irradiation treatment. The rotation angle is the angle at which the table surface of the treatment room table is planned to rotate counterclockwise (or clockwise) on a plane parallel to the ground when the patient is undergoing irradiation treatment. The original target point cloud is the three-dimensional image data obtained by extracting the surface contour of multi-frame cross-sectional computer tomography (CT) images of the irradiated target, which contains the surface contour information of the irradiated target.

Figure 3:
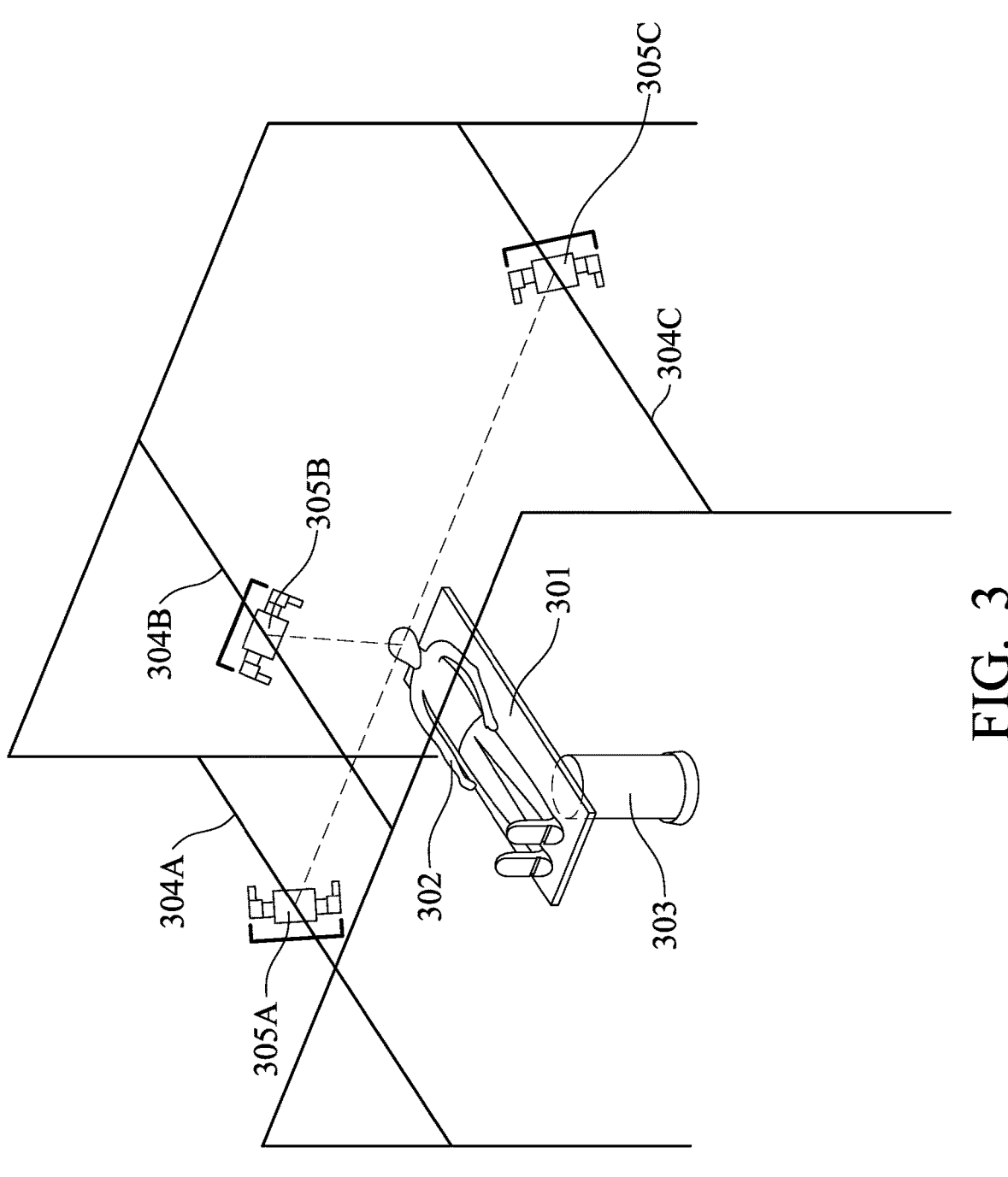
FIG. 3 is a schematic diagram of an exemplary hardware configuration of the positioning room, according to an embodiment of the present disclosure.

FIG. 3 is a schematic diagram illustrating an exemplary hardware configuration of the positioning room 300, according to an embodiment of the present disclosure. As shown in FIG. 3, the hardware configuration of the positioning room 300 may include the configuration of the positioning room table (i.e., the table in the positioning room) 301, a set of camera devices 305A-305C (hereinafter referred to as "the first set of camera devices") and slide rails 304A-304C.

The positioning room table 301 can be supported by the base column 303, so that the patient 302 carried by the positioning room table 301 has a certain height from the ground. In addition, the positioning room table 301 is foldable, so it can be tilted upwards, and the patient 302 can even be in a sitting position. In an embodiment, the positioning room table 301 can be tilted but not rotated. In another embodiment, the positioning room table 301 can be tilted and rotated.

The camera devices 305A, 305B, and 305C can be any kind of depth cameras, which are respectively installed on the right side, upper side and left side of the positioning room table 301 to capture images of the affected part of the patient 302 from different angles. By reconstructing the images of these affected parts, the point cloud information of the irradiation target can be obtained.

The camera devices 305A, 305B, and 305C are mounted on the slide rails 304A, 304B and 304C respectively, and the slide rails 304A, 304B, and 304C allow the camera devices 305A, 305B, and 305C to move on them respectively. In addition, laser emitters though not shown in FIG. 3) are attached to the camera devices 305A, 305B, and 305C, for aim at the affected part of the patient 302 (i.e., the irradiation target), so that the spatial relationship between the irradiation target and the first set of camera devices can be learned. In addition, since the positions of the slide rails 304A, 304B, and 304C are fixed, the relative position of the affected part of the patient 302 in the space of the positioning room 300 can be determined based on the positions of the first set of cameras on the slide rails when the laser emitters aim at the affected part of the patient 302 (e.g., moved backward by 10 centimeters relative to the origin).

Figure 4:
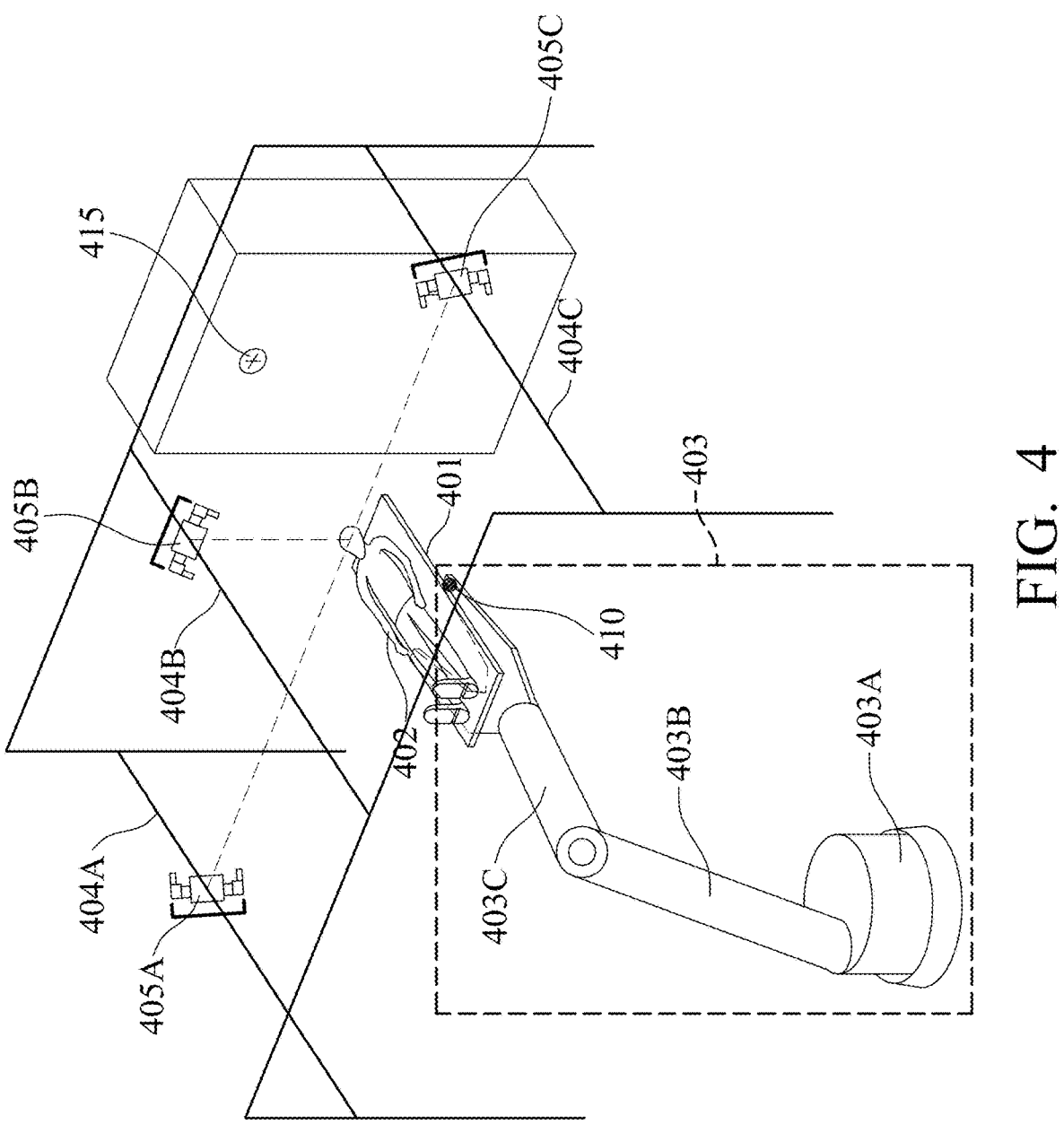
FIG. 4 is a schematic diagram of an exemplary hardware configuration of a treatment room, according to an embodiment of the present disclosure.

FIG. 4 is a schematic diagram illustrating an exemplary hardware configuration of a treatment room 400, according to an embodiment of the present disclosure. As shown in FIG. 4, the hardware configuration of the treatment room 400 may include a treatment room table 401, a mechanical device 403, a set of camera devices 405A-405C (hereinafter referred to as "second set of camera devices"), slide rails 404A-404C, and beam exit 415.

The mechanical device 403 may include a base part 403A, a support part 403B, and an arm part 403C. The arm part 403C is used for supporting the treatment room table 401 and the patient 402 thereon. The support part 403B is used for supporting the arm part 403C. The base part 403A is used for supporting the arm part 403C and the support part 403B. The base 403A may include a controller (though not shown in FIG. 4) for controlling the tilt angles of the support part 403B and the arm part 403C, so as to change (raise or lower) the height of the treatment room table 401.

Like the positioning room table 301, the treatment room table 401 also has foldability, so it can be tilted upwards, and even the patient 402 can be in a sitting position. In addition, the arm part 403C of the mechanical device 403 is connected to the treatment room table 401 through a rotating flange or similar elements at the fulcrum 410. In addition to connecting the mechanical device 403 to the treatment room table 401, the rotating flange also allows the arm 403C to rotate the treatment room table 401.

The camera devices 405A, 405B, and 405C can be any kind of depth cameras, which are respectively installed on the right side, upper side, and left side of the treatment room table 401 to capture images of the affected part of the patient 402 from different angles. By reconstructing these images of the affected area, the point cloud of the irradiated target can be obtained.

The camera devices 405A, 405B, and 405C are mounted on the slide rails 404A, 404B, and 404C respectively, and the slide rails 404A, 404B, and 404C allow the camera devices 405A, 405B, and 405C to move on them respectively. In addition, laser emitters (although not shown in FIG. 4) are attached to the camera devices 405A, 405B, and 405C for aiming at the affected part of the patient 402, so that the spatial relationship between the irradiation target and the second set of camera devices can be learned.

FIG. 3 and FIG. 4 are respectively the hardware configurations during the execution of the positioning room positioning process 203 and the treatment room positioning process 204. During the positioning room calibration process 201 and the treatment room calibration process 202, the positioning room table 301 and the treatment room table 401 are not loaded with patients, but a calibration object (or "calibration jig") is placed as the simulation of the patient's affected part, for calibrating the parameters and spatial relative positions of the camera devices in the positioning room and treatment room.

Figure 5:
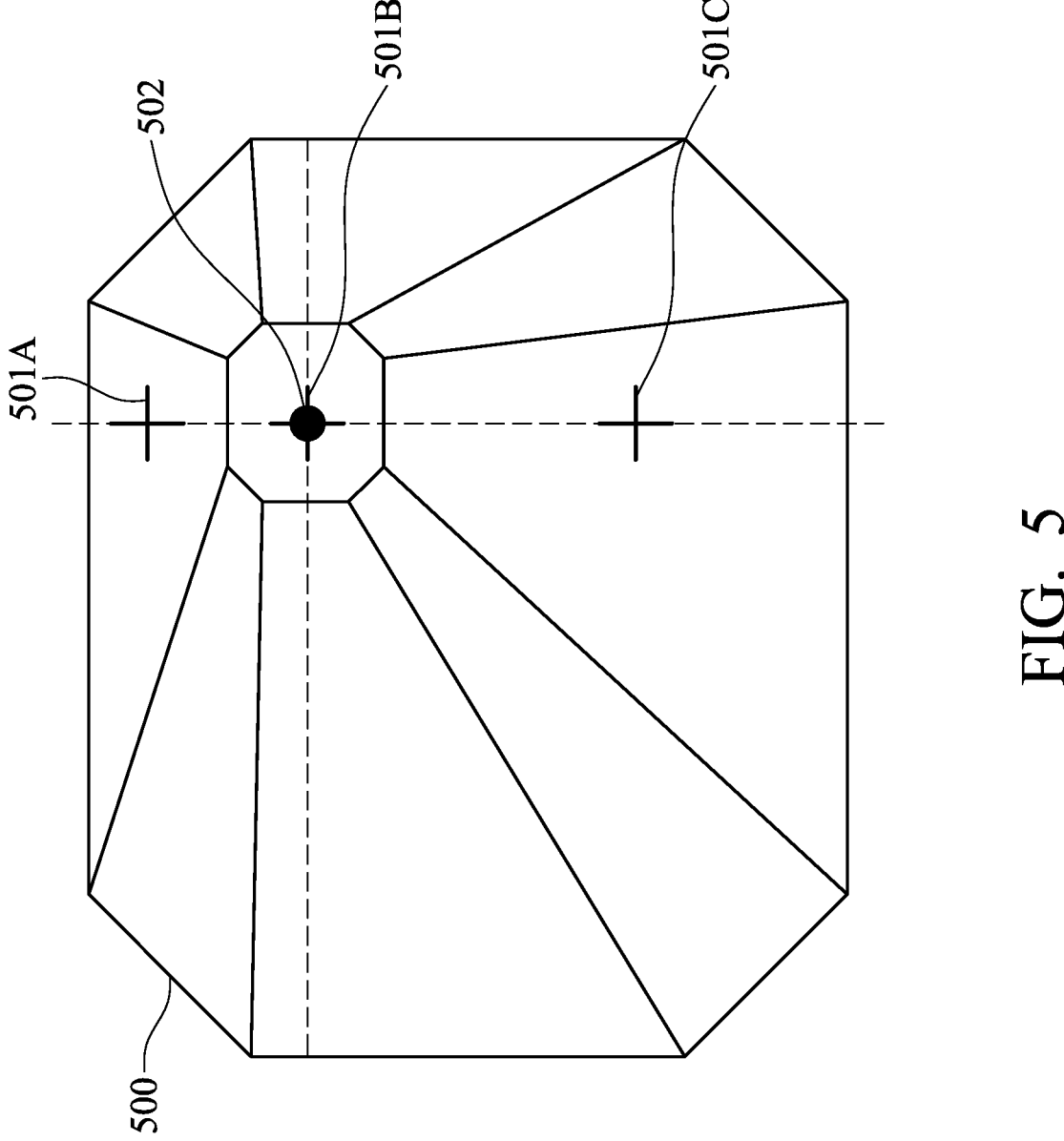
FIG. 5 is a top view of a calibration object that relates to the positioning room calibration process and the treatment room calibration process, according to an embodiment of the present disclosure.

FIG. 5 is a top view of a calibration object 500 that relates to the positioning room calibration process 201 and the treatment room calibration process 202, according to an embodiment of the present disclosure. As shown in FIG. 5, the calibration object 500 is a three-dimensional object with crosshairs 501A, 501B, and 501C on it, which are respectively for the laser emitters attached to the camera devices 305A, 305B, and 305C (or camera devices 405A, 405B, and 405C) to aim. When the laser emitters attached to the camera set are all aligned with the crosshairs 501A, 501B, and 501C, the extension of the laser beam emitted by these laser emitters is expected to pass through the isocenter 502 of the calibration object 500.

It should be appreciated that FIG. 5 is only an example, and the appearance of the calibration object 500 is not limited by the embodiments of the present disclosure.

FIG. 6 is a flow diagram illustrating the positioning room positioning process 203 of the first implementation, according to an embodiment of the present disclosure. In this implementation, the positioning room table 301 in the positioning room 300 cannot rotate. As shown in FIG. 6, the positioning room positioning process 203 may include steps 601-605.

In step 601, the tilt target point cloud is calculated based on the tilt angle and the original target point cloud. Then, the positioning room positioning process 203 proceeds to step 602.

In an embodiment, the calculation in step 601 is to obtain the tilt target point cloud by multiplying each point coordinate on the original target point cloud by the first transformation matrix that corresponds to the tilt angle.

In step 602, the first captured point cloud of the irradiation target on the positioning room table 301 captured by the first set of camera devices when the positioning room table 301 is tilted at the tilt angle is obtained. Then, the positioning room positioning process 203 proceeds to step 603.

In step 603, the first offset is determined by performing image registration on the tilt target point cloud and the first captured point cloud. Then, the positioning room positioning process 203 proceeds to step 604.

In an embodiment, the image registration performed in step 603 includes calculating the similarity between the tilt target point cloud and the first captured point cloud. If the similarity is insufficient, then the position of the first set of camera devices on the slide rails 304A-304C is adjusted (manually or electronically controlled), and the first captured point cloud is re-captured. The above operations are repeated until the similarity between the captured first captured point cloud and the tilt target point cloud falls within an acceptable range. At this moment, the difference between the current position and the starting position of the first set of camera devices on the slide rails 304A-304C is the first offset.

In step 604, the first support displacement of the fulcrum 410 relative to the beam exit 415 when the treatment room table 401 is tilted at the tilt angle but not rotated is calculated based on the first offset, the target displacement, and the reference displacement. Then, the positioning room positioning process 203 proceeds to step 605.

In an embodiment, the calculation in step 604 is to obtain the first support displacement by adding the first offset, the target displacement, and the reference displacement.

In step 605, the second support displacement is calculated based on the rotation angle and the first support displacement.

FIG. 7 is a flow diagram of a treatment room positioning process 204, according to an embodiment of the present disclosure. As shown in FIG. 7, the treatment room positioning process 204 may include steps 701-705.

In step 701, the mechanical device 403 is driven to move the treatment room table 401, such that the fulcrum 410 is at the first support displacement relative to the beam exit 415. Then, the treatment room positioning process 204 proceeds to step 702.

In step 702, the second captured point cloud of the irradiation target on the treatment room table 401 captured by the second set of camera devices when the treatment room table 401 is tilted at the tilt angle is obtained. Then, the treatment room positioning process 204 proceeds to step 703.

In step 703, the second offset is determined by performing image registration on the tilt target point cloud and the second captured point cloud. Then, the treatment room positioning process 204 proceeds to step 704.

In an embodiment, the image registration performed in step 703 includes calculating the similarity between the tilt object point cloud and the second captured point cloud. If the similarity is insufficient, the mechanical device 403 is driven to move the treatment room table 401, and the second captured point cloud is re-captured. The above operations are repeated until the similarity between the second captured point cloud and the tilt target point cloud falls within an acceptable range. At this moment, the difference between the current position and of the fulcrum 410 and the position of fulcrum 410 in step 402 (i.e. the position at the first support displacement relative to the beam exit 415) is the second offset.

In step 704, the second support displacement is corrected based on the rotation angle and the second offset. Then, the treatment room positioning process 204 proceeds to step 705.

In step 705, the mechanical device 403 is driven to move the treatment room table 401, such that the fulcrum 410 of the treatment room table 401 is at the second support displacement relative to the beam exit 415.

FIG. 8 is a flow diagram of the positioning room positioning process 203R in the second implementation, according to another embodiment of the present disclosure. In the second implementation, the positioning room table 301 in the positioning room 300 can rotate. As shown in FIG. 8, the positioning room positioning process 203R may include steps 801-804.

In step 801, the transformed target point cloud is calculated based on the tilt angle, the rotation angle, and the original target point cloud. Then, the positioning room positioning process 203R proceeds to step 802.

In an embodiment, the calculation in step 801 is to the transformed target point cloud by multiplying the coordinates of each point on the original target point cloud by the first transformation matrix and the second transformation matrix. The first transformation matrix and the second transformation matrix correspond to the tilt angle and the rotation angle, respectively.

In step 802, the third captured point cloud of the irradiation target on the positioning room table 301 captured by the first set of camera devices when the positioning room table 301 is tilted at the tilt angle and rotated at the rotation angle is obtained. Then, the positioning room positioning process 203R proceeds to step 803.

In step 803, a third offset is determined by performing image registration on the transformed target point cloud and the third captured point cloud. Then, the positioning room positioning process 203R proceeds to step 804.

In an embodiment, the image registration performed in step 803 includes calculating the similarity between the transformed target point cloud and the third captured point cloud. If the similarity is insufficient, then the position of the first set of camera devices on the slide rails 304A-304C is adjusted (manually or electronically controlled), and the third captured point cloud is re-captured. The above operations are repeated until the similarity between the third captured point cloud and the transformation target point cloud falls within an acceptable range. At this moment, the difference between the current position and the starting position of the first set of the camera devices on the slide rails 304A-304C is the third offset.

In step 804, the second support displacement is calculated based on the third offset, the target displacement and the reference displacement.

In an embodiment, the calculation in step 804 is to obtain the second support displacement by adding the third offset, the target displacement, and the reference displacement.

Figure 9:
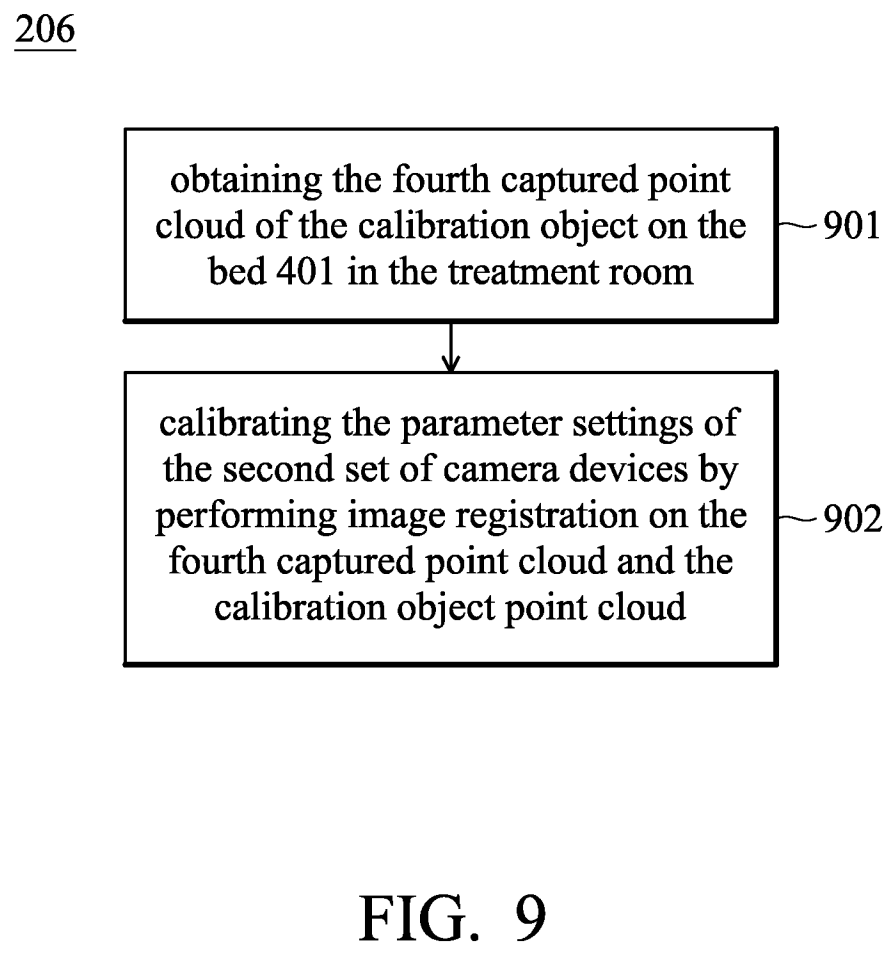

FIG. 9 is a flow diagram of the camera parameter calibration process 206, according to an embodiment of the present disclosure. As shown in FIG. 9, the camera parameter calibration process 206 may include step 901 and step 902.

In step 901, the fourth captured point cloud of the calibration object 500 on the table 401 in the treatment room captured by the second set of camera devices is obtained. Then, the camera parameter calibration process 206 proceeds to step 902.

In step 902, by performing image registration on the fourth captured point cloud and the calibration object point cloud, the parameter settings of the second set of camera devices are calibrated.

In an embodiment, the image registration performed in step 902 includes calculating the similarity between the calibration object point cloud and the fourth captured point cloud. If the similarity is insufficient, then the parameters of the second set of camera devices are adjusted. The above operations are repeated until the similarity between the captured fourth captured point cloud and the calibration object point cloud falls within an acceptable range.

Figure 10:
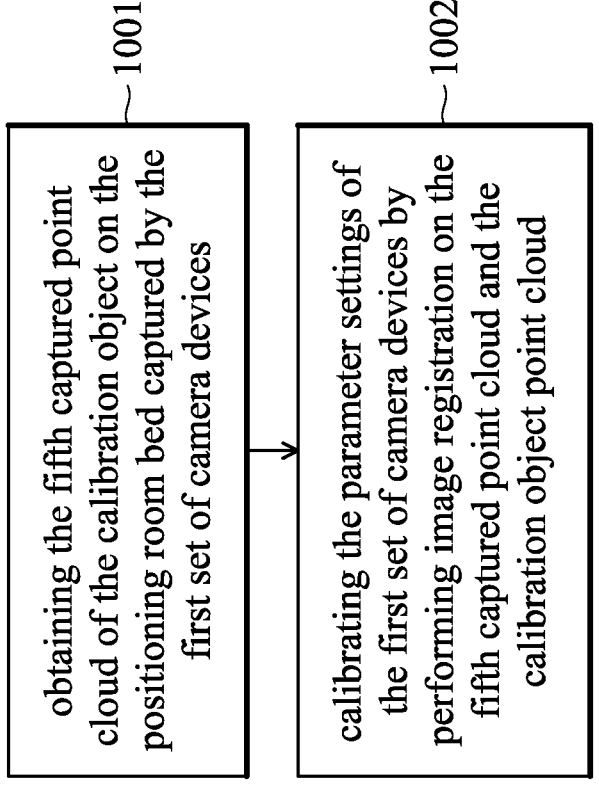
FIG. 10 is a flow diagram of a positioning room calibration process, according to an embodiment of the present disclosure.

FIG. 10 is a flow diagram of a positioning room calibration process 201, according to an embodiment of the present disclosure. As shown in FIG. 10, the calibration room calibration process 201 may include step 1001 and step 1002.

In step 1001, the fifth captured point cloud of the calibration object 500 on the positioning room table 301 captured by the first set of camera devices is obtained. Then, the calibration room calibration process 201 proceeds to step 1002.

In step 1002, by performing image registration on the fifth captured point cloud and the calibration object point cloud, the parameter settings of the first set of camera devices are calibrated.

In an embodiment, the image registration performed in step 1002 includes calculating the similarity between the calibration object point cloud and the fifth captured point cloud. If the similarity is insufficient, then the parameters of the first set of camera devices are adjusted. The above operations are repeated until the similarity between the fifth captured point cloud and the calibration object point cloud falls within an acceptable range.

Figure 11:
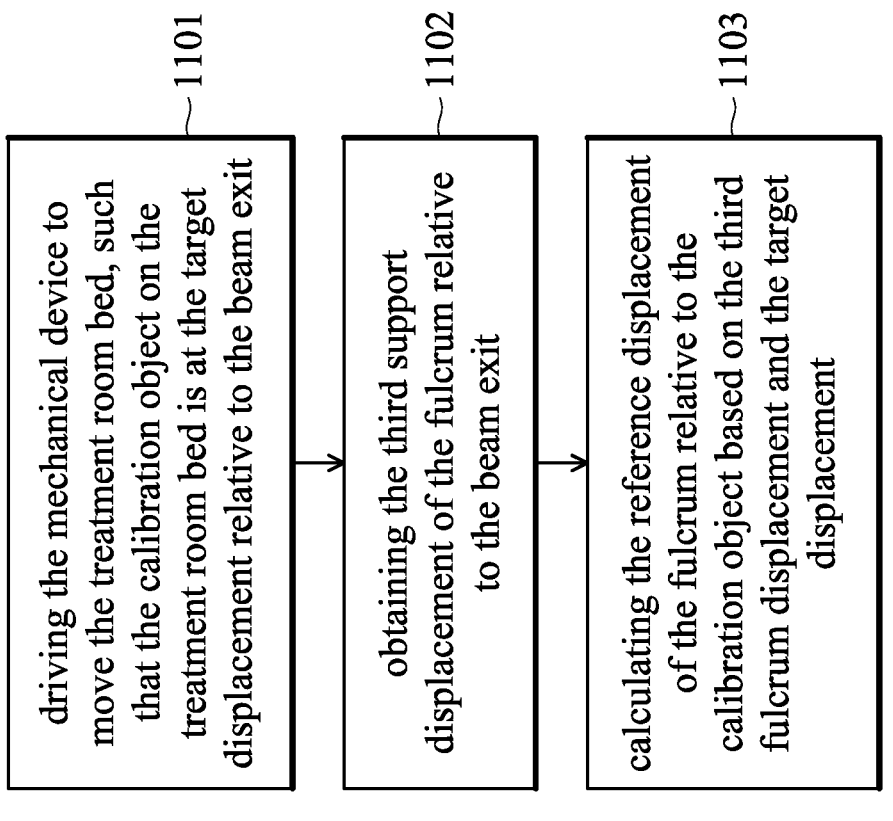
FIG. 11 is a flow diagram of the spatial calibration process, according to an embodiment of the present disclosure.

FIG. 11 is a flow diagram of the spatial calibration process 205, according to an embodiment of the present disclosure. As shown in FIG. 11, the spatial calibration process 205 may include steps 1101-1103.

In step 1101, the mechanical device 403 is driven to move the treatment room table 401, such that the calibration object 500 on the treatment room table 401 is at the target displacement relative to the beam exit 415. Then, the spatial calibration process 205 proceeds to step 1102.

In step 1102, the third support displacement of the fulcrum 410 relative to the beam exit 415 is obtained. Then, the spatial calibration process 205 proceeds to step 1103.

In step 1103, the reference displacement of the fulcrum 410 relative to the calibration object 500 is calculated based on the third support displacement and the target displacement.

The described operation of making the positioning room table 301 and/or the treatment room table 401 tilt at the tilt angle and/or rotate at the rotation angle can be manually manipulated or electronically controlled, the present disclosure is not limited thereto.

In various embodiments, when the configuration of the treatment room table conforms to the treatment planning data, the treatment room table is tilted at the tilt angle and rotated at the rotation angle, and the irradiation target on the treatment room table is at the target displacement relative to the beam exit.

The patient-positioning system provided in the present disclosure increases the consideration and adjustment of the tilt and rotation angle of the patient table/chair and the irradiation direction, enabling more efficient and accurate irradiation of the patient's affected part in the context of radiotherapy.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A patient-positioning system for radiotherapy, comprising a processing device and a storage device, wherein the processing device loads a program from the storage device to execute:

a control module, obtaining treatment planning data, wherein the treatment planning data includes a tilt angle, a rotation angle, a target displacement, and an original target point cloud of an irradiation target;

a positioning room module, calculating a first support displacement of a fulcrum through image registration based on the tilt angle, the rotation angle, the target displacement, the original target point cloud, and a reference displacement, wherein the first support displacement is a displacement of the fulcrum relative to a beam exit when arrangement of a treatment room table conforms to the treatment planning data, and wherein the treatment room table and a mechanical device are connected at the fulcrum; and a treatment room module, driving the mechanical device to move the treatment room table such that the fulcrum is at the first support displacement relative to the beam exit;

wherein when the arrangement of the treatment room table conforms to the treatment planning data, the treatment room table is tilted at the tilt angle and rotated at the rotation angle, and the irradiation target on the treatment room table is at the target displacement relative to the beam exit.

2. The system as claimed in claim 1, wherein the positioning room module further executes the following steps:

calculating a tilt target point cloud based on the tilt angle and the original target point cloud;

obtaining a first captured point cloud of the irradiation target on the positioning room table, wherein the first captured point cloud is captured by a first set of camera devices when the positioning room table is tilted at the tilt angle;

determining a first offset by performing image registration on the tilt target point cloud and the first captured point cloud;

calculating a second support displacement of the fulcrum based on the first offset, the target displacement, and the reference displacement, wherein the second support displacement is the displacement of the fulcrum relative to the beam exit when the treatment room table is tilted at the tilt angle but not rotated; and calculating the first support displacement based on the rotation angle and the second support displacement.

3. The system as claimed in claim 2, wherein the treatment room module further executes the following steps:

driving the mechanical device to move the treatment room table such that the fulcrum is at the second support displacement relative to the beam exit;

obtaining a second captured point cloud of the irradiation target on the treatment room table, wherein the second captured point cloud is captured by a second set of camera devices when the treatment room table is tilted at the tilt angle;

determining a second offset by performing image registration on the tilt target point cloud and the second captured point cloud; and correcting the first support displacement based on the rotation angle and the second offset.

4. The system as claimed in claim 3, wherein the treatment room module further executes the following steps:

obtaining a fourth captured point cloud of a calibration object on the treatment room table, wherein the fourth captured point cloud is captured by the second set of camera devices; and calibrating parameter settings of the second set of camera devices by performing image registration on the fourth captured point cloud and a calibration object point cloud;

wherein a second set of laser emitters are attached to the second set of camera devices; and wherein when the second set of camera devices captures the fourth captured point cloud, laser beams emitted by the second set of laser emitters are aligned with the corresponding marks on the calibration object.

5. The system as claimed in claim 1, wherein the positioning room module further executes the following steps:

calculating a transformed target point cloud based on the tilt angle, the rotation angle and the original target point cloud;

obtaining a third captured point cloud of the irradiation target on the positioning room table, wherein the third captured point cloud is captured by the first set of camera devices when the positioning room table is tilted at the tilt angle and rotated at the rotation angle;

determining a third offset by performing image registration on the transformed target point cloud and the third captured point cloud; and calculating the first support displacement based on the third offset, the target displacement, and the reference displacement.

6. The system as claimed in claim 2, wherein the positioning room module further executes the following steps:

obtaining a fifth camera point cloud of a calibration object on the positioning room table, wherein the fifth camera point cloud is captured by the first set of camera devices; and calibrating parameter settings of the first set of camera devices by performing image registration on the fifth captured point cloud and the calibration object point cloud;

wherein a first set of laser emitters are attached to the first set of camera devices; and wherein when the first set of camera devices captures the fifth captured point cloud, laser beams emitted by the first set of laser emitters are aligned with corresponding crosshairs on the calibration object.

7. The system as claimed in claim 1, wherein the treatment room module further executes the following steps:

driving the mechanical device to move the treatment room table such that the calibration object on the treatment room table is at the target displacement relative to the beam exit;

obtaining a third support displacement of the fulcrum relative to the beam exit; and calculating the reference displacement of the fulcrum relative to the calibration object based on the third support displacement and the target displacement.

8. The system as claimed in claim 1, wherein the treatment room module further drives an irradiation device to irradiate the irradiation target on the treatment room table.

9. The system as claimed in claim 5, wherein the positioning room module further executes the following steps:

obtaining a fifth camera point cloud of a calibration object on the positioning room table, wherein the fifth camera point cloud is captured by the first set of camera devices; and calibrating parameter settings of the first set of camera devices by performing image registration on the fifth captured point cloud and the calibration object point cloud;

wherein a first set of laser emitters are attached to the first set of camera devices; and wherein when the first set of camera devices captures the fifth captured point cloud, laser beams emitted by the first set of laser emitters are aligned with corresponding crosshairs on the calibration object.

\* \* \* \* \*